United States Patent
Frolov et al.

(10) Patent No.: US 10,487,041 B2
(45) Date of Patent: Nov. 26, 2019

(54) METHOD FOR PRODUCING N-METHYL-PARA-ANISIDINE

(71) Applicant: OBSCHESTVO S OGRANICHENNOI OTVETSTVENNOSTYU "IFOTOP", Moscow (RU)

(72) Inventors: Alexandr Yurievich Frolov, Moscow (RU); Nikolay Grigorievich Belyakov, Moscow (RU)

(73) Assignee: OBSCHESTVO S OGRANICHENNOI OTVETSTVENNOSTYU "IFOTOP", Moscow (RU)

( * ) Notice: Subject to any disclaimer, the term of this patent is extended or adjusted under 35 U.S.C. 154(b) by 0 days.

(21) Appl. No.: 16/330,775

(22) PCT Filed: Sep. 12, 2016

(86) PCT No.: PCT/RU2016/000569
§ 371 (c)(1),
(2) Date: Mar. 6, 2019

(87) PCT Pub. No.: WO2018/048320
PCT Pub. Date: Mar. 15, 2018

(65) Prior Publication Data
US 2019/0241500 A1    Aug. 8, 2019

(30) Foreign Application Priority Data
Sep. 7, 2016    (RU) ................................. 2016134238

(51) Int. Cl.
C07C 209/24    (2006.01)
C07C 217/84    (2006.01)
C07C 209/84    (2006.01)

(52) U.S. Cl.
CPC .......... *C07C 209/24* (2013.01); *C07C 209/84* (2013.01); *C07C 217/84* (2013.01)

(58) Field of Classification Search
None
See application file for complete search history.

(56) References Cited

U.S. PATENT DOCUMENTS 4,952,734 A    8/1990    Weber et al.

FOREIGN PATENT DOCUMENTS

| GB | 428092 A1 | 12/1933 |
| RU | 2270831 C1 | 2/2006 |
| RU | 2285691 C1 | 10/2006 |
| RU | 2508288 C1 | 2/2014 |
| SU | 802264 | 2/1981 |

*Primary Examiner* — Clinton A Brooks
(74) *Attorney, Agent, or Firm* — Dmitry S. Kryndushkin

(57) ABSTRACT

The invention relates to chemical engineering processes, and more particularly to liquid-phase catalytic methods for producing, in the presence of hydrogen, alkylated para-anisidine for use as a chemical substance or as a gasoline additive for increasing the octane rating of a gasoline. The technical result of the claimed group of inventions is an increase in the yield of N-methyl-para-anisidine and a decrease in the yield of a dimethyl derivative. A method for producing N-methyl-para-anisidine in a liquid phase includes alkylating para-anisidine with formalin as they are separately, simultaneously fed into a mixer disposed in a reactor, directly upstream of a catalytic reduction zone, thus producing an intermediate azomethine, and subsequently reducing same on a hydrogenation catalyst at a temperature of 20-120° C. in an environment of hydrogen at elevated pressure, and then isolating the target product, N-methyl-para-anisidine.

8 Claims, No Drawings

METHOD FOR PRODUCING N-METHYL-PARA-ANISIDINE

FIELD OF THE INVENTION

The invention relates to chemical technological processes and, in particular, to liquid-phase catalytic methods for producing alkylated para-anisidine in the presence of hydrogen, and use of para-anisidine as a chemical or additive to gasoline to increase its octane number.

BACKGROUND OF THE INVENTION

There is a known method for liquid-phase catalytic alkylation of aniline, disclosed in RU 2270831 C1, publ. 27 Feb. 2006. The method involves the alkylation of aniline in the presence of hydrogen and a fixed palladium catalyst in ethyl or methyl alcohol at a temperature of 55-65° C. and a pressure of 0.2-0.4 MPa. In this case, alkylation is carried out with formalin at aniline:formalin ratio of 1.6/1.1, the process is carried out in a cylindrical reactor mounted on a rocking chair with a swing number of 120-160 $min^{-1}$, in the middle part of which is placed a porous block cellular palladium catalyst, active layer of which is modified by palladium nanoparticles, with a porosity of 70-95% and a palladium content of 1.8-3.7%, with hydrogen being fed through the fitting of the reactor lid.

The disadvantage of the prior art method is the low yield of N-methylanilian (not more than 55%).

The closest analogue of the claimed invention is a method of liquid-phase catalytic alkylation of aromatic amines, disclosed in RU 2285691 C1, publ. 20 Oct. 2006. The method includes the alkylation of aromatic amines on a heterogeneous catalyst in the presence of hydrogen and lower alcohols at a temperature of 50-70° C. Alkylation is carried out with formalin in a reactor with a reaction zone filled with a catalyst consisting of a block highly porous cellular alumina carrier with a porosity in the 70-95% and the active component, which is palladium with a mass content equal to 1.3-2.0%.

The disadvantage of the closest analogue is the low yield of N-methylanilian (not above 57%).

Alkylation of para-anisidine under the conditions described in patent RU 2285691 resulted in a similar, low yield of N-methyl-para-anisidine and high values of the dimethyl derivant, which does not allow to consider this method acceptable for industrial production of the desired product N-methyl-para-anisidine.

SUMMARY OF THE INVENTION

The goal of the claimed group of inventions is to develop a method for producing N-methyl-para-anisidine, which makes it possible to obtain N-methyl-para-anisidine in a yield of over 70% and a minimum value of its dimethyl derivant.

The technical result of the claimed group of inventions is to increase yield of N-methyl-para-anisidine and reduce yield of the dimethyl derivant.

Indicated technical result is achieved by the method for producing N-methyl-para-anisidine in a liquid phase, comprising the alkylation of a solution of para-anisidine with formalin in a separate, simultaneous flow in a mixer located in a reactor immediately before a catalytic reduction zone with formation of the intermediate azomethine-4-methoxy-(N-phenylmethanimine), followed by its reduction on a hydrogenation catalyst at a temperature of 20-120° C., preferably 75-85° C., in the presence of hydrogen at an elevated pressure of 0.1-100 ATMG preferably 5-10 ATMG and the subsequent selection of the target product—N-methyl-para-anisidine.

There is applied formalin containing 28-30 wt % of formaldehyde, the use of more concentrated solutions leads to clogging of the mixer formed by azomethine and less concentrated solutions leads to increasing the amount of ballast water.

Formalin containing 28-30 wt % formaldehyde should be used, the use of more concentrated solutions leads to clogging of the mixer by the resulting azomethine, and less concentrated solutions will increase the amount of ballast water.

The alkylation process is carried out in batch or in continuous mode.

In alkylation, stabilizers may be used in the amount of 5-10 mol. % of the pair-anisidine load. Triethylamine, tetramethylethylenediamine, diisopropylethylamine, dimethylbenzylamine, diazabicyclooctane, tripropylamine, an aqueous solution of trimethylamine are preferably used as tertiary aliphatic amines.

In alkylation, stabilizers may be used in the form of aqueous solutions of sodium and potassium hydroxides of diluted or concentrated lower limiting acids, such as formic, acetic, propionic, and their sodium and potassium salts.

The stabilizer is introduced into the reactor during loading of the hydrogenation catalyst and/or during supply of a para-anisidine solution.

The hydrogenation catalyst is used as a suspension or as a fixed bed.

The solution of para-anisidine is obtained by dissolving it in a solvent selected from the simplest aliphatic alcohols, such as methanol, ethanol, isopropanol, etc. The preferred concentration of para-anisidine in the solution is 15-35 mol. %.

A suspension of the hydrogenation catalyst is obtained by stirring it in a reactor with a solvent selected from the simplest aliphatic alcohols, such as methanol, ethanol, isopropanol, etc.

The separation of N-methyl-para-anisidine is carried out by fractional distillation.

The stabilizer is recovered from the catalyzate by simple distillation or fractional distillation, with subsequent reuse.

As a hydrogenation catalyst, it is possible to use metals of the VIII group, such as nickel, cobalt, pure iron (skeletal catalysts) or on carriers such as kieselgur, coal, alumina, silicates, etc.

The hydrogenation catalyst may be metals selected from the platinum group (Ru, Rh, Pd, Os, Ir, Pt), including metals deposited on the above-mentioned carriers.

The hydrogenation catalyst can be Raney copper or copper on the above-mentioned carriers.

The hydrogenation catalysts disclosed above can be modified with titanium, chromium, tungsten and other metals.

The method allows for conducting the process in a stirred reactor or column type apparatus.

DETAILED DESCRIPTION OF THE INVENTION

The preferred variant of the invention is disclosed hereby. The method for producing N-methyl-para-anisidine in a liquid phase is carried out by alkylation of para-anisidine with formalin in a reactor, which is an autoclave operating in batch mode and made of steel X18H10T, with a capacity of 0.5 l, equipped with a high-speed turbine agitator with a screened electric drive, jacket for the coolant, thermocouple sleeve, the upper loading and lower unloading fittings. The temperature was measured with a potassium chlorate thermocouple placed in a sleeve built into the lid of the autoclave, and its registration was carried out using the "Oven" temperature control device UKT38-Sch4. The hydrogen absorption was monitored by a manometer. The autoclave was equipped with two consumable, glass, calibrated burettes with a capacity of 200 ml, a double-flow micropump (MMC type, Czech Republic) with adjustable flow rates in both streams and automatic maintenance of the flow ratio in the flows. The loading fitting cover was replaced with a special one, fitted with two metal nozzles of 3 mm diameter, welded into it, provided for separate supply of para-anisidine and formalin. From the inside of the lid, two nozzles were combined into one, forming a mixer for mixing two streams of para-anisidine and formalin.

Burettes were connected to a double-flow pump and then fluoroplastic tubes with a mixer, designed for pressures up to 50 at.

A hydrogenation catalyst was charged into the prepared autoclave in an amount of 5-20 mass % of the para-anisidine loading and enough methanol to achieve the level of the stirrer blades. The autoclave loading nozzle was closed with a mixing cap. One of burettes was filled with formalin in the amount of 16-20 wt. % of the free working volume of the reactor, to another para-anisidine or its solution in the amount of 32-60 wt. % of the free working volume of the reactor (depending on the concentration of para-anisidine), asked the flow rates of raw materials, based on the calculation of the full, simultaneous emptying of burettes during 1 hour. Automatic tracking system for the flow ratio was switched on, the pump was switched on. After the full filling of PTFE tubes, the pump was turned off and these tubes were connected to the mixer. If necessary, stabilizers were loaded into the autoclave, preferably in an amount of 5-10 mol. % of the pair-anisidine load. A stabilizer is introduced into the reactor when the hydrogenation catalyst is charged and/or when para-anisidine is supplied.

The autoclave was sealed and purged with nitrogen to remove air from it and then hydrogen to displace nitrogen. After that, the hydrogen pressure in the autoclave was set at 0.1-100 atm., temperature setting 20-120° C. and included a thermostat. Upon reaching the set temperature in the autoclave, the stirrer drive and the micropump were switched on. Formalin and para-anisidine or its solution was pumped from burettes to the mixer, where the streams were mixed and para-anisidine interacted with formaldehyde to form a water-methanol solution of Schiff base (azomethine)-4-methoxy-(N-phenylmethanimine) the concentration of the latter, preferably 8.8-12.7 mol. % and molar ratio of components Schiff base:methanol:water=1:(2-5):(4.9-5.3). The resulting solution of azomethine in the form of droplets came from the mixer to the catalyst, for example, a suspension of Raney nickel in methanol, where it was rapidly hydrogenated to form a secondary amine. The flow rate control in the flows was carried out with the help of burettes, by decreasing the liquid level for certain periods of time.

After the reagents were completely exhausted from the burettes (approximately 1 hour), the pump was turned off, the shutter speed was given for 0.5 hours, after which the heating of the autoclave and the stirrer were turned off. The autoclave, if necessary, was cooled to +35° C., the catalyst was discharged through the bottom and cartridge filter into the receiving tank.

Methanol, water and low-boiling impurities were distilled off from the obtained catalyzate at atmospheric pressure, the remaining mass was distilled off at a residual pressure of 20 mm Hg Received the product composition: N-methyl-para-anisidine, N, N-dimethyl-para-anisidine, para-anisidine. Then from the resulting composition during rectification the target product was isolated—N-methyl-para-anisidine.

The reactor can also operate in continuous mode. In contrast to the batch mode, for the implementation of a continuous alkylation process, the autoclave was additionally equipped with a metal-ceramic nickel filter on the riser for sampling and a control valve at the fitting for sampling in order to continuously organize the process. A filter that blocks the catalyst exit from the autoclave was set at about % the height of the autoclave. After emptying the burettes, the process was not stopped, but was again poured over with a solution of para-anisidine and formalin, and this operation was periodically repeated as needed. The autoclave was gradually filling up. After about 1.5 hours, the first drops of catalyzate appeared on the discharge nozzle of the control valve, which were sent to the receiving tank, like all subsequent ones. After 75 hours of continuous operation, the process was planned to be stopped with high catalyst activity. After that, the catalyzate was discharged from the autoclave and combined with the catalyzate selected through the control valve.

The reaction temperature mainly affects its speed and its choice depends on the task and equipment.

Example 1

A prepared autoclave with a capacity of 400 cm$^3$ was charged with 5 g of Raney nickel and 100 ml of methanol, which corresponds to 10 wt. % of the pair-anisidine load. The autoclave loading nozzle was closed with a mixing cap. In one of the burettes there was poured 40.87 g of formalin containing 29.8 wt. % formaldehyde, which corresponds to the mass of 18.2% of the free working volume of the reactor, to another solution 50 g of para-anisidine in 80 ml of methanol, which corresponds to 59 wt. % of the free working volume of the reactor and the concentration of para-anisidine in a solution of 44.1 wt. % (17 mol. %), asked the flow rates of raw materials, based on the calculation of the full, simultaneous emptying of burettes for 1 hour. Automatic tracking system for the flow ratio was switched on, the pump was switched on. After the full filling of PTFE tubes, the pump was turned off and these tubes were connected to the mixer.

The autoclave was sealed and purged with nitrogen to remove air from it and then with hydrogen for nitrogen displacement, creating hydrogen pressure of 5 atm, the temperature was set to +80° C. and included a thermostat. Upon reaching the set temperature in the autoclave, the stirrer drive and the micropump were switched on. Formalin and the para-anisidine solution were pumped from burettes to the mixer, where the streams were mixed and para-anisidine reacted with formaldehyde to form a water-methanol solution of Schiff base (azomethine)-4-methoxy-(N-phenylmethanimine). The resulting solution of 4-methoxy-(N-phenylmethanimine) with a molar ratio of components Schiff base:methanol:water=1:4.88:4.92 in the form of droplets came from the mixer to a suspension of Raney nickel in methanol, where it was rapidly hydrogenated to form a secondary amine. The flow rate control in the flows was carried out with the help of burettes, by decreasing the liquid level for certain periods of time.

After the reagents were completely exhausted from the burettes (approximately 1 hour), the pump was turned off, the shutter speed was given for 0.5 hours, after which the heating of the autoclave and the stirrer were turned off. The autoclave was cooled to +35° C., the catalyst was discharged through the bottom and cartridge filter into the receiving tank.

Methanol, water and low-boiling impurities were distilled off from the obtained catalyzate at atmospheric pressure, the remaining mass was distilled off at a residual pressure of 20 mm Hg Received 53.48 g of the product of the composition: N-methyl-para-anisidine—75.44%, N, N-dimethyl-para-anisidine—17.85%, para-anisidine—6.7%.

The output of N-methyl-para-anisidine—72.44%

Example 2

This example reveals the continuous operation of the autoclave, which corresponds to the operation of the autoclave of example 1, but the autoclave was additionally equipped with a nickel and ceramic-metal sintered filter on the riser for sampling and a control valve at the sampling nozzle for the purpose of continuous process organization. A filter that blocks the catalyst exit from the autoclave was set at about the height of the autoclave.

After loading the initial components of example 1, the pressure of hydrogen was set to 5 atm on the control valve and then acted as in Example 1, but after emptying the burettes, the process was not stopped, but they were again poured with para-anisidine and formaldehyde solutions and this operation was periodically repeated as necessary. The autoclave was gradually filling up.

After about 1.5 hours, the first drops of catalyzate appeared on the discharge nozzle of the control valve, which were sent to the receiving tank, like all subsequent ones. After 75 hours of continuous operation, the process was stopped. Discharge of catalyzate from the autoclave was produced, as in example 1 and combined it with catalyzate selected through the control valve.

After distillation of catalyzate as in Example 1, 4135.07 g of composition product were obtained: N-methyl-para-anisidine—78.0%, N, N-dimethyl-para-anisidine—12.812%, para-anisidine—9.88%.

The output of N-methyl-para-anisidine—77.2%.

Example 3

In a tube with a diameter of 25 mm and a height of 500 mm, made of stainless steel X18H10T, equipped with a mixer underneath, as in Example 2 and a fitting for hydrogen supply, an upper control valve, a jacket for heating with hot water and a thermocouple sleeve, the Raney nickel catalyst with pieces of 3-5 mm size in an amount of 250 ml. The mixer, as in example 2, was connected to the fluoroplastic tubes to the burette-pump system, the hydrogen fitting was connected to the hydrogen line.

The temperature was set at +80° C. on the thermostat and the pressure on the control valve was 5 atm, the thermostat was turned on. When the set temperature was reached, the pump was turned on, as in Example 2, and the hydrogen supply. The total consumption of liquid components was 1 hour$^{-1}$ and hydrogen 0.3 min$^{-1}$. Liquid reaction products were collected in the collection. They worked continuously for 75 hours.

After distillation of the catalyzate, a product of 6068.49 g was obtained: N-methyl-para-anisidine-80.2%, N, N-dimethyl-para-anisidine—10.25%, para-anisidine—9.54%.

The yield of N-methyl-para-anisidine is 79.2%.

Example 4

The method for producing N-methyl-para-anisidine in example 4 corresponds to example 1, except that 0.41 g of a triethylamine stabilizer was added to a methanol solution of para-anisidine (1 mol. % of the pair-anisidine load).

After completion of the process, methanol was distilled off from the obtained catalyzate together with triethylamine, which were sent for reuse, then water and low-boiling impurities at atmospheric pressure, the remaining mass was distilled off at a residual pressure of 20 mm Hg.

There was received 54.69 g of the product composition: N-methyl-para-anisidine—81.3%, N, N-dimethyl-para-anisidine—11.5%, para-anisidine—7.2%.

The yield of N-methyl-para-anisidine is 79.7%.

This example shows that when adding a stabilizer is less than 5 mol. % of the para-anisidine load, the yield of dimethyl derivative increases.

Example 5

The method for producing N-methyl-para-anisidine according to example 5 corresponds to example 4, except that 2.05 g of a triethylamine stabilizer (5 mol. % of the pair-anisidine load).

There was received 54.6 g of the product composition: N-methyl-para-anisidine—85.6%, N, N-dimethyl-para-anisidine—7.6%, para-anisidine—6.8%.

The yield of N-methyl-para-anisidine is 83.8%.

Example 6

A method for producing N-methyl-para-anisidine of example 6 corresponds to example 4, except that a methanolic solution of para-anisidine was added 4.1 g of triethylamine stabilizer (10 mol. % of the pair-anisidine load).

There was received 54.58 g of the product composition: N-methyl-para-anisidine—88.4%, N, N-dimethyl-para-anisidine—5.5%, para-anisidine—6.1%.

The yield of N-methyl-para-anisidine is 86.6%.

Example 7

A method for producing N-methyl-para-anisidine of example 7 corresponds to example 4, except that a methanolic solution of para-anisidine was added 6.15 gof triethylamine stabilizer (15 mol. % of the pair-anisidine load).

There was received 54.59 g of the product composition: N-methyl-para-anisidine—87.6%, N, N-dimethyl-para-anisidine—6.0%, para-anisidine—6.4%.

The yield of N-methyl-para-anisidine is 85.8%.

The example shows that the addition of a stabilizer is more than 10 mol. % does not lead to a further increase in product yield and a decrease in dimethyl derivative.

Example 8

A method for producing N-methyl-para-anisidine of example 8 corresponds to example 1 except that the autoclave to a methanolic suspension of Raney nickel catalyst were added 4.1 g of triethylamine (10 mol. % of the pair-anisidine load).

There was received 54.61 g of the product composition: N-methyl-para-anisidine—85.5%, N, N-dimethyl-para-anisidine—7.6%, para-anisidine—6.9%.

The yield of N-methyl-para-anisidine is 83.7%.

Example 9

A method for producing N-methyl-para-anisidine of example 9 corresponds to example 1, except that a methanolic solution of para-anisidine and the autoclave were added in equal proportions, a total of 4.1 g of triethylamine (10 mol. % molar from loading para-anisidine).

There was received 54.2 g of the product composition: N-methyl-para-anisidine—89.4%, N, N-dimethyl-para-anisidine—6.1%, para-anisidine—4.5%.

The output of N-methyl-para-anisidine 87.0%.

Example 10

A method for producing N-methyl-para-anisidine of example 10 corresponds to example 1, except that a methanolic solution of para-anisidine and the autoclave were added in equal proportions, a total of 4.72 g of tetramethylethylenediamine (10 mol. % molar from loading para-anisidine).

There was received 54.43 g of the product composition: N-methyl-para-anisidine—91.6%, N, N-dimethyl-para-anisidine—2.8%, para-anisidine—5.6%.

The yield of N-methyl-para-anisidine was 89.5%.

Example 11

A method for producing N-methyl-p-anisidine of example 11 corresponds to example 1, except that a methanolic solution of para-anisidine and the autoclave were added in equal proportions, a total of 5.16 g of diisopropylethylamine (10 mol. % of the para-anisidine load).

There was received 55.2% of product composition: N-methyl-para-anisidine—76.1%, N, N-dimethyl-para-anisidine—8.0%, para-anisidine—15.9%.

The yield of N-methyl-para-anisidine is 75.4%.

Example 12

A method for producing N-methyl-p-anisidine of example 12 corresponds to example 1, except that a methanolic solution of para-anisidine and the autoclave were added in equal proportions, a total of 5.48 g of dimethylbenzylamine (10 mol. % of the pair-anisidine load).

There was received 55.57 g of the product composition: N-methyl-para-anisidine—93.4%, N, N-dimethyl-para-anisidine—2.2%, para-anisidine—4.4%.

The yield of N-methyl-para-anisidine is 93.2%.

Example 13

A method for producing N-methyl-para-anisidine of example 13 corresponds to example 11 except that instead of hydrogenating Raney nickel catalyst, 1 wt. % palladium on coal was used.

There was received 55.25 g of the product composition: N-methyl-para-anisidine—90.1%, N, N-dimethyl-para-anisidine—5.4%, para-anisidine—4.5%.

The yield of N-methyl-para-anisidine was 89.4%.

Example 14

A method for producing N-methyl-para-anisidine of example 14 corresponds to example 12, except that 3 wt. % palladium on coal was used.

There was received 55.5 g of the product composition: N-methyl-para-anisidine—94.5%, N, N-dimethyl-para-anisidine—1.9%, para-anisidine—3.6%.

The yield of N-methyl-para-anisidine was 94.2%.

Example 15

A method for producing N-methyl-para-anisidine of example 15 corresponds to example 11 except that instead of Raney nickel was used 54 wt. % nickel on kizelgur.

There was received 55.57 g of the product composition: N-methyl-para-anisidine—92.2%, N, N-dimethyl-para-anisidine—2.4%, para-anisidine—5.4%.

The yield of N-methyl-para-anisidine was 92.0%.

Table 1 presents some of the characteristic results on the outputs of N-methyl-para-anisidine and dimethyl derivatives, obtained in the implementation of the claimed method.

As it can be seen from table 1, the claimed method allows for obtaining a high yield of the target product—N-methyl-para-anisidine and reduce the yield of by-products—dimethyl derivatives.

Thus, the invention allows for obtaining a high-liquid, liquid-phase method for producing a monoalkylated product—N-methyl-para-anisine, with a yield of more than 70.

The invention was disclosed above with reference to a specific embodiment thereof. Other embodiments of the invention that do not change its nature, as disclosed herein, may be apparent to those skilled in the art. Accordingly, the invention should be considered limited in scope only by the following claims.

TABLE 1

| No | Stabilizer | Hydrogen pressure, atm | Temperature in the reactor, °C. | Concentration, mol. % in PA solution | Concentration, mol. % in catalyst suspension | The yield of the target product in percent, % | The output of dimethyl derivatives |
|---|---|---|---|---|---|---|---|
| 1 | prototype | 5 | 80 | | | 54.74 | 29.962 |
| 2 | Without stabilizer | | | | | 74.54 | 17.85 |
| 3 | Triethylamine (TEA) | | | 1 | 0 | 79.7 | 11.5 |
| 4 | TEA | | | 5 | 0 | 83.8 | 7.6 |
| 5 | TEA | | | 10 | 0 | 86.6 | 5.5 |
| 6 | TEA | | | 15 | 0 | 85.8 | 6.0 |
| 7 | TEA | | | 0 | 10 | 83.7 | 7.6 |
| 8 | TEA | | | 5 | 5 | 87.0 | 5.94 |

TABLE 1-continued

| No | Stabilizer | Hydrogen pressure, atm | Temperature in the reactor, °C | Concentration, mol. % in PA solution | Concentration, mol. % in catalyst suspension | The yield of the target product in percent, % | The output of dimethyl derivatives |
|---|---|---|---|---|---|---|---|
| 9 | Tetramethylethylenediamine (TMED) | | | 5 | 5 | 89.5 | 2.7 |
| 10 | Diisopropylethylamine (DIEA) | | | 5 | 5 | 75.4 | 8.0 |
| 11 | Dimethylbenzylamine (DMBA) | | | 5 | 5 | 93.2 | 2.2 |
| 12 | DMBA | | | 5 | 5 | 94.2 | 1.9 |
| 13 | Without stabilizer | 0.1 | 120 | — | — | 70.3 | 24.7 |
| 14 | Without stabilizer | 100 | 20 | — | — | 76.1 | 13.4 |

The invention claimed is:

1. A method for producing N-methyl-para-anisidine in a liquid phase, comprising alkylating para-anisidine with formalin as they are separately, simultaneously fed into a mixer disposed in a reactor, directly upstream of a catalytic reduction zone, thus producing an intermediate azomethine-4-methoxy-(N-phenylmethanimine), and subsequently reducing said intermediate on a hydrogenation catalyst at a temperature of 20-120° C., in an environment of hydrogen at elevated pressure, and then separating the target product, N-methyl-para-anisidine, wherein para-anisidine is used in the form of a solution in a solvent selected from the group: ethanol, methanol, isopropanol.

2. The method according to claim 1, wherein the alkylation is carried out in a batch mode.

3. The method according to claim 1, wherein the alkylation is carried out on in a continuous mode.

4. The method according to claim 1, wherein stabilizers are used during the alkylation in the form of tertiary aliphatic amines, wherein said stabilizers are used in the amount of 5-10 mol. % of the para-anisidine load.

5. The method according to claim 4, wherein tertiary aliphatic amines are selected from the group: triethylamine, tetramethylethylenediamine, diisopropylethylamine, dimethylbenzylamine, diazabicyclooctane, tripropylamine, aqueous solution of trimethylamine.

6. The method according to claim 4, wherein the stabilizer is introduced into the reactor during loading of the hydrogenation catalyst and/or during supply of para-anisidine.

7. The method according to claim 1, wherein the hydrogenation catalyst is used in the form of a suspension or in the form of a fixed layer.

8. The method according to claim 1, wherein the separation of N-methyl-para-anisidine is carried out by fractional distillation.

* * * * *